US00PP37629P2

(12) United States Plant Patent
van Dijk

(10) Patent No.: US PP37,629 P2
(45) Date of Patent: Aug. 18, 2026

(54) ***ANTHURIUM* PLANT NAMED 'AN2950768'**

(50) Latin Name: *Anthurium andreanum*
Varietal Denomination: AN2950768

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/323,769

(22) Filed: Sep. 9, 2025

(51) Int. Cl.
*A01H 5/02* (2018.01)
*A01H 6/10* (2018.01)

(52) U.S. Cl.
USPC ..... Plt./365
CPC ..... *A01H 6/10* (2018.05)

(58) Field of Classification Search
USPC ..... Plt./365
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Anthurium* plant named 'AN2950768', characterized by its tall, upright to somewhat outwardly arching plant habit; suitable for cut flower production; narrowly cordate dark green-colored leaves; freely flowering habit; open inflorescences that are positioned above the foliar plane on strong scapes; large broadly cordate-shaped spathes that are white and light yellow green in color with reddish venation and margins; and yellowish white and yellow green-colored spadices.

3 Drawing Sheets

Figure 1:
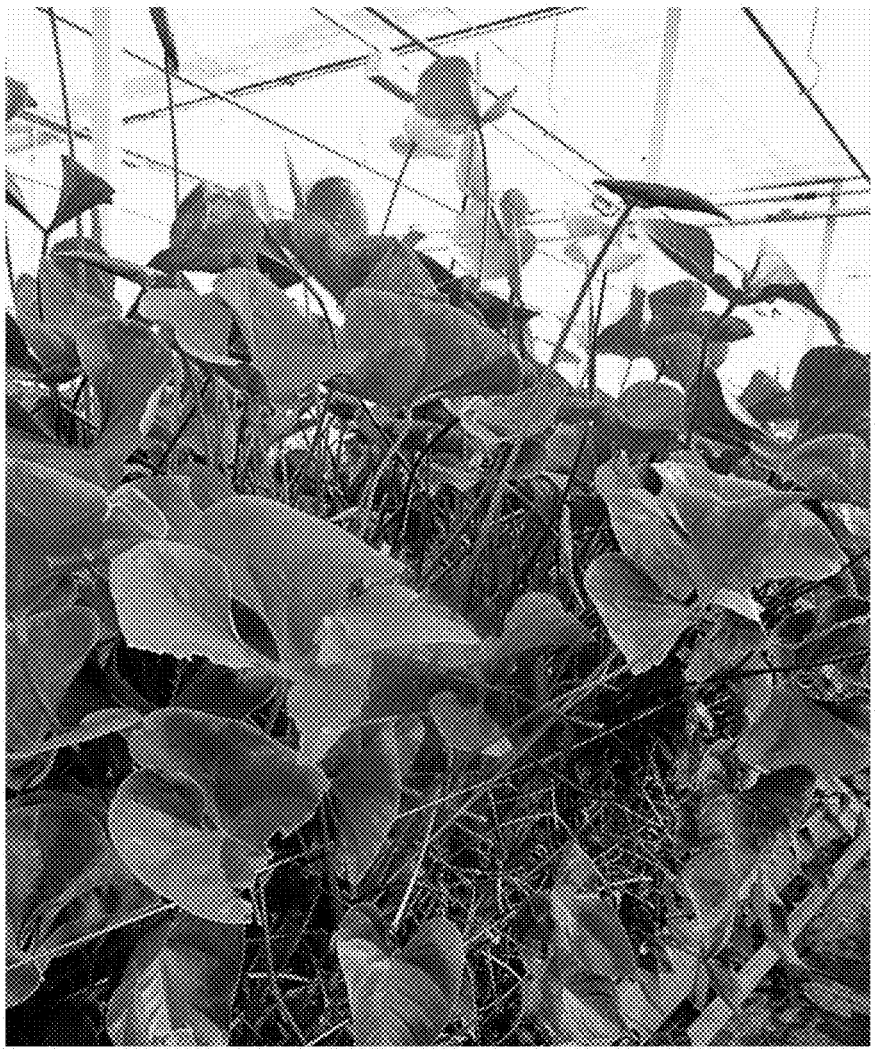

Botanical designation: *Anthurium andreanum.*
Cultivar denomination: 'AN2950768'.

CROSS-REFERENCED TO CLOSELY-RELATED APPLICATION

A European Community Plant Breeder's Rights application for the instant plant was filed by the Applicant/Assignee of the instant application, Anthura B.V. of Bleiswijk, The Netherlands on Nov. 20, 2024, application number 2024/2681. Foreign priority is not claimed to this application.

BACKGROUND OF THE INVENTION

The present invention relates to a new and distinct cultivar of *Anthurium* plant, botanically known as *Anthurium andreanum,* commonly referred to as Flamingo Flower and hereinafter referred to by the name 'AN2950768'.

The new *Anthurium* plant is a product of a controlled breeding program conducted by the Inventor in Bleiswijk, The Netherlands. The objective of the breeding program is to create new *Anthurium* plants suitable to be produced as cut flowers with durable and uniquely-colored spathes.

The new *Anthurium* plant originated from a cross-pollination made by the Inventor in December 2007 in Bleiswijk, The Netherlands of a proprietary breeding selection of *Anthurium andreanum* identified as code number 04-010595-0001, not patented, as the female, or seed, parent with a proprietary breeding selection of *Anthurium andreanum* identified as code number 04-010538-0004, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in December 2010.

Asexual reproduction of the new *Anthurium* plant by in vitro meristem propagation in a controlled environment in Bleiswijk, The Netherlands since March 2015 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2950768'. These characteristics in combination distinguish 'AN2950768' as a new and distinct *Anthurium* plant:

1. Tall, upright to somewhat outwardly arching plant habit; suitable for cut flower production.
2. Narrowly cordate dark green-colored leaves.
3. Freely flowering habit.
4. Open inflorescences that are positioned above the foliar plane on strong scapes.
5. Large broadly cordate-shaped spathes that are white and light yellow green in color with reddish venation and margins.
6. Yellowish white and yellow green-colored spadices.

Plants of the new *Anthurium* differ primarily from plants of the female parent selection in the following characteristics:

1. Spathes of plants of the new *Anthurium* are white and light yellow green in color with reddish venation and margins whereas spathes of plants of the female parent selection are yellow green in color.

2. Spadices of plants of the new *Anthurium* are yellowish white and yellow green in color whereas spadices of plants of the female parent selection are light pink in color.

Plants of the new *Anthurium* differ primarily from plants of the male parent selection in the following characteristics:

1. Spathes of plants of the new *Anthurium* are broader than spathes of plants of the male parent selection.
2. Spathes of plants of the new *Anthurium* are white and light yellow green in color with reddish venation and margins whereas spathes of plants of the male parent selection are white in color.
3. Spadices of plants of the new *Anthurium* are yellowish white and yellow green in color whereas spadices of plants of the male parent selection are yellow in color.

Plants of the new *Anthurium* can also be compared to plants of *Anthurium andreanum* 'ANTHIUFEN', not patented. In side-by-side comparisons, plants of the new *Anthurium* differ primarily from plants of ANTHIUFEN' in the following characteristics:

1. Spathes of plants of the new *Anthurium* are white and light yellow green in color with reddish venation and margins whereas spathes of plants of 'ANTHIUFEN' are white in color flushed with green towards the basal lobes and with light green-colored venation.
2. Spathe apices of plants of the new *Anthurium* are abruptly acute with long mucronate apices whereas spathe apices of plants of 'ANTHIUFEN' are narrowly acute.
3. Scapes of plants of the new *Anthurium* are more heavily tinged with anthocyanin than scapes of plants of 'ANTHIUFEN'.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of typical plants of 'AN2950768' grown in a nursery bed.

Figure 2:
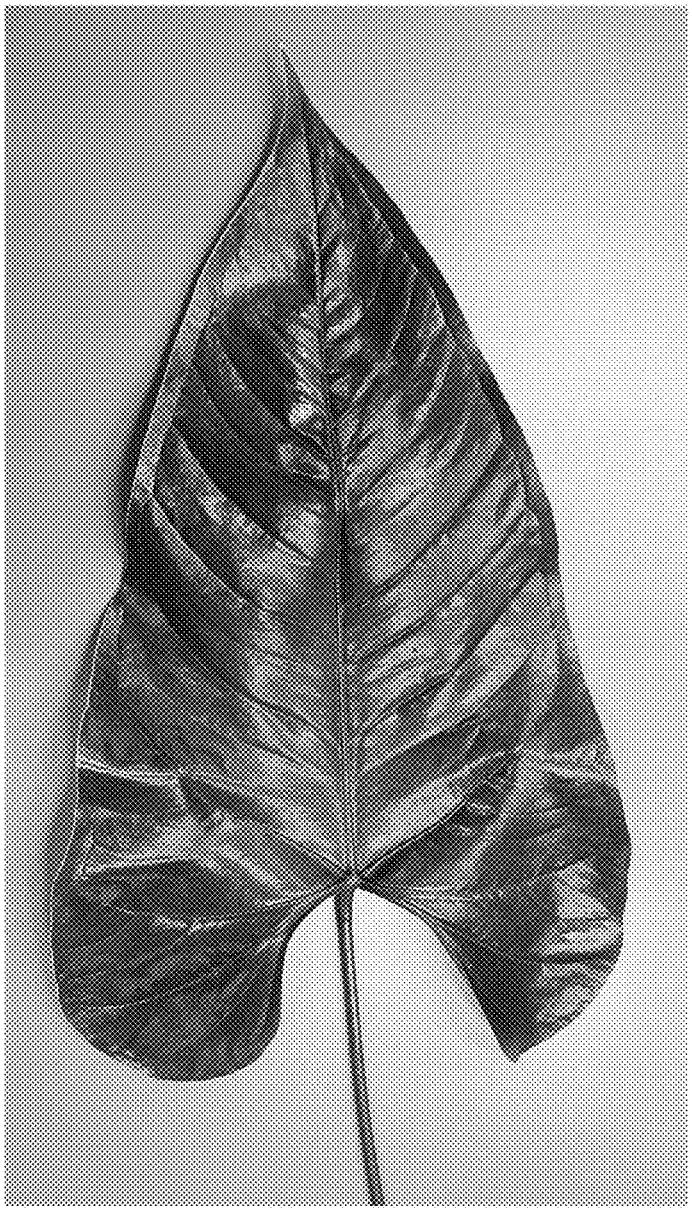

The photograph on the second sheet (FIG. 2) is a close-up view of a typical leaf of 'AN2950768'.

Figure 3:
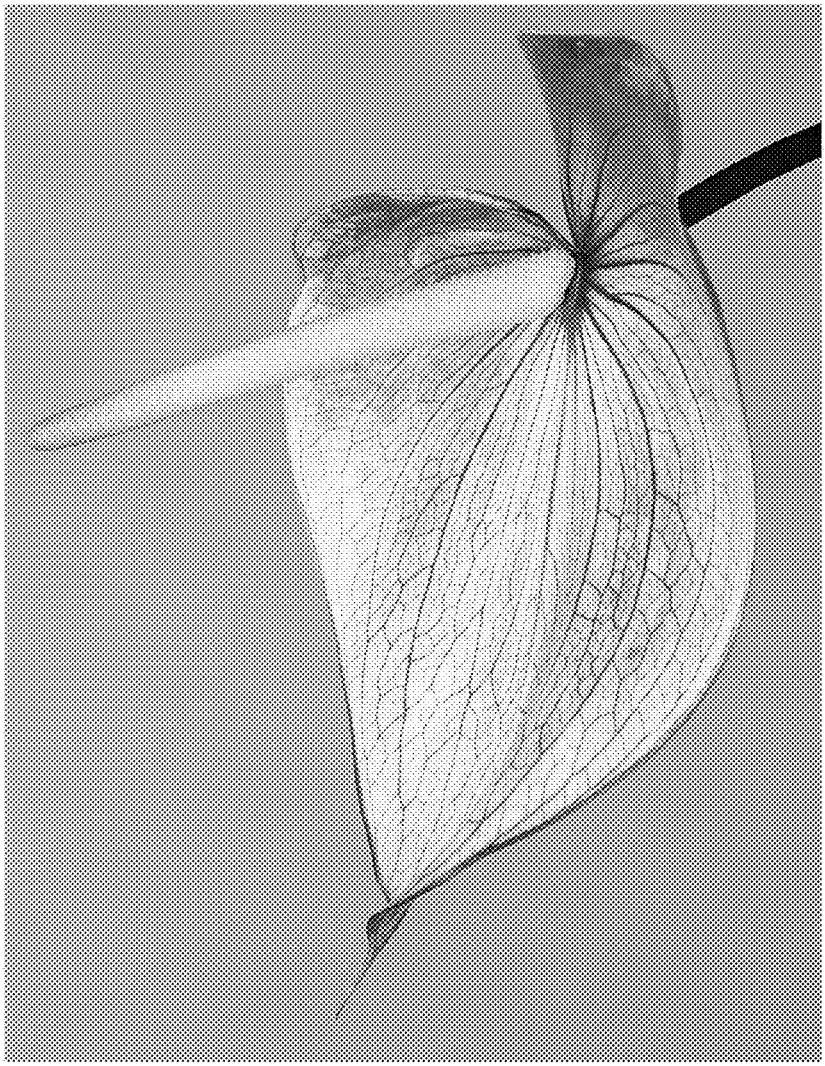

The photograph on the third sheet (FIG. 3) is a close-up view of a typical inflorescence of 'AN2950768'.

DETAILED BOTANICAL DESCRIPTION

The aforementioned photographs and following observations and measurements describe plants grown in nursery beds during the winter in a glass-covered greenhouse in Bleiswijk, The Netherlands. Plants were grown under conditions and practices which approximate those generally used in commercial *Anthurium* cut flower production. During the production of the plants, day and night temperatures ranged from about 19° C. to about 22.5° C. and light levels ranged from about 100 μmol to about 200 μmol. Plants were six years from planting young rooted plants when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2950768'.

Parentage:

*Female, or seed, parent*.—Proprietary breeding selection of *Anthurium andreanum* identified as code number 04-010595-0001, not patented.

*Male, or pollen, parent*.—Proprietary breeding selection of *Anthurium andreanum* identified as code number 04-010538-0004, not patented.

Propagation:

*Type*.—By in vitro meristem propagation.

*Time to initiate roots, summer and winter*.—About two weeks at temperatures ranging from about 19° C. to about 22.5° C.

*Time to produce a rooted young plant, summer and winter*.—About six to eight weeks at temperatures ranging from about 19° C. to about 22.5° C.

*Root description*.—Medium in thickness, fibrous; typically light yellow green in color; actual color of the roots is dependent on substrate composition, water quality, fertilizer type and formulation, substrate temperature and physiological age of roots.

*Rooting habit*.—Freely branching, medium density.

Plant description:

*Plant shape and growth habit*.—Tall, upright to somewhat outwardly arching plant habit; overall shape, narrowly obovate; moderately vigorous growth habit and moderate growth rate.

*Cut flower productivity*.—In a single year of production, about seven flowering stems can be harvested per plant.

*Plant height, from soil level to top of leaf plane*.—About 125 cm.

*Plant height, from soil level to top of inflorescences*.—About 156 cm.

*Plant diameter or spread*.—About 97 cm.

*Cut flower description*.—Stem length: About 77.7 cm. Stem diameter: About 2.8 cm. Aspect: Upright. Strength: Strong. Color, developing: Close to a blend of 145C and 149C. Color, developed: Close to 145B to 145C.

Leaf description:

*Arrangement*.—Alternate; simple.

*Length*.—About 36.6 cm.

*Width*.—About 23.1 cm.

*Shape*.—Narrowly cordate.

*Apex*.—Apiculate with a mucronate tip.

*Base*.—Deeply cordate to shallowly auriculate

*Margin*.—Entire; moderately to strongly coarsely undulate.

*Texture, upper and lower surfaces*.—Smooth, glabrous; moderately coriaceous.

*Venation pattern*.—Pinnate.

*Color*.—Developing leaves, upper and lower surfaces: Close to 152A tinged with close to N199A; midvein, close to 144A. Fully expanded leaves, upper surface: Close to a blend of NN137A and 147A; venation, close to 178A. Fully expanded leaves, lower surface: Close to 146A; venation, close to 144B and 144C and proximally close to 178A.

*Petioles*.—Length: About 65.5 cm. Diameter: Distally, about 5 mm and proximally, about 10 mm. Texture, upper and lower surfaces: Smooth, glabrous. Color, upper surface: Close to 200B; moderately covered with fine dots, close to 153C. Color, lower surface: Close to 146A and 146B; moderately covered with fine dots, close to 145A. Geniculum length: About 3.6 cm. Geniculum diameter: About 7 mm. Geniculum texture, upper and lower surfaces: Smooth, glabrous. Geniculum color, upper surface: Close to 200B; moderately covered with fine dots, close to 164B and 164C. Geniculum color, lower surface: Close to 143A. Wing length: About 8.7 cm. Wing diameter: About 1 cm. Wing texture: Smooth, glabrous. Wing color: Close to 144A; towards the margins, close to 144C; with subsequent development, strongly tinged with close to 176A.

Inflorescence description:

*Inflorescence arrangement and flowering habit.*—Spathes with spadices; open inflorescences held above the foliar plane on strong scapes; flowering structures arise from leaf axils; freely and continuous flowering year-round in controlled temperature greenhouses in The Netherlands; typically about two developing and developed inflorescences per plant at one time; inflorescence development commences about 18 months after planting rooted young plants.

*Inflorescence longevity.*—As a cut flower, spathes maintain good substance for about four to five weeks; on the plant, inflorescences last for about two months; inflorescences persistent.

*Fragrance.*—Very faint; sweet and pleasant.

*Spathes.*—Length: About 19.8 cm. Width: About 16.1 cm. Shape: Broadly cordate; slightly concave. Apex: Abruptly acute with a long mucronate apex. Base: Cordate. Margin: Entire; slightly and coarsely undulate. Aspect: About 115° from the scape axis. Texture, upper and lower surfaces: Smooth, glabrous; moderately coriaceous. Color: When developing, front surface: Close to 145B; towards the base, close to 144A and 144B; towards the apex, close to 157D; narrow marginal edges, close to 152C and 152D; distal edges, close to 149B. When developing, rear surface: Close to 146D; towards the base, close to 144B; towards the apex, close to 157C and 157D; narrow marginal edges, close to 152C and 152D; distal edges, close to 144B. Fully developed, front surface: Close to 145C and 145D; towards the base, close to 145A; towards the apex, close to 155C; apex, close to 182D and 161C; narrow marginal edges, close to 175C; main veins, close to 175A to 175C, distally, closer to 178B; secondary veins, close to 143A to 143B. Fully developed, rear surface: Close to 157A and 157B; towards the base, close to 147D; towards the apex, close to 155C; apex, close to 182D and 162A; narrow marginal edges, close to N170A; main veins, close to 148A, distally, closer to 180B; secondary veins, close to 146D.

*Spadices.*—Length: About 10.6 cm. Diameter: Proximally, about 12 mm; distally, about 8 mm. Shape: Cylindrical, slightly tapering towards the apex; apex, obtuse; base, obtuse; in cross-section, rounded. Aspect: About 7.5° from the scape axis. Color, immature: Close to 151C; distally, close to 145B. Color, mature: Close to 158C; distally, close to 146D. Flowers: Type: Hermaphroditic. Quantity per spadix: About 800. Height: About 0.75 mm. Diameter: About 2 mm. Shape: Roughly square. Anther color: Close to 158C. Pollen amount: Scarce. Pollen color: Close to 155B. Stigma color: Close to 157D.

*Scapes.*—Length: About 78.2 cm. Diameter: About 8 mm. Strength: Strong, sturdy. Aspect: About 30° from vertical. Color: Close to a blend of 166A and 200B; moderately covered with fine dots, close to 147D; at proximal and distal ends, tinged with close to 143A and 143B.

*Seed and fruit.*—To date, seed and fruit development has not been observed on plants of the new *Anthurium.*

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures of about 30° C. and to be hardy to USDA Hardiness Zone 10.

It is claimed:

1. A new and distinct *Anthurium* plant named 'AN2950768' as herein illustrated and described.

* * * * *